United States Patent
Johnson et al.

(10) Patent No.: US 12,042,154 B2
(45) Date of Patent: Jul. 23, 2024

(54) WINDLASS TOURNIQUET

(71) Applicants: TACTICAL MEDICAL SOLUTIONS, LLC, Anderson, SC (US); Ross A. Johnson, Anderson, SC (US); Richard Alan Hester, Greenville, SC (US); Cory S. Husley, Anderson, SC (US)

(72) Inventors: Ross A. Johnson, Anderson, SC (US); Richard Alan Hester, Greenville, SC (US); Cory S. Hulsey, Anderson, SC (US)

(73) Assignee: Tactical Medical Solutions, LLC, Anderson, SC (US)

( * ) Notice: Subject to any disclaimer, the term of this patent is extended or adjusted under 35 U.S.C. 154(b) by 350 days.

(21) Appl. No.: 17/609,715

(22) PCT Filed: May 8, 2020

(86) PCT No.: PCT/US2020/032254
§ 371 (c)(1),
(2) Date: Nov. 8, 2021

(87) PCT Pub. No.: WO2020/227697
PCT Pub. Date: Nov. 12, 2020

(65) Prior Publication Data
US 2022/0218359 A1    Jul. 14, 2022

Related U.S. Application Data (60) Provisional application No. 62/845,051, filed on May 8, 2019.

(51) Int. Cl.
*A61B 17/132* (2006.01)
*A61B 17/00* (2006.01)

(52) U.S. Cl.
CPC ....... *A61B 17/1327* (2013.01); *A61B 2017/00367* (2013.01); *A61B 2017/00477* (2013.01)

(58) Field of Classification Search
CPC .............. A61B 17/132; A61B 17/1322; A61B 17/1327; A61B 2017/00477
See application file for complete search history.

(56) References Cited

U.S. PATENT DOCUMENTS

| | | | |
|---|---|---|---|
| 8,343,182 B2 * | 1/2013 | Kirkham | A61B 17/1322 606/203 |
| 10,016,203 B2 * | 7/2018 | Esposito | A61B 17/1327 |

(Continued)

*Primary Examiner* — Ryan J. Severson
(74) *Attorney, Agent, or Firm* — CAHN & SAMUELS, LLP (57) ABSTRACT

Present invention is directed to a tourniquet having a base including at least first and second sections and having a cap attached to one of the sections. A compression strap is attached to the base and extends across the base. A windlass handle is provided and includes a strap aperture through which the compression strap is threaded through and stitched to itself. A locking strap extends across and is attached to the cap. A handle stop engages the locking strap such that the handle stop freely slides along the handle strap. A strap connector assembly is provided and includes a buckle frame and a self-cinching sliding arm transversely extending from a first side of the buckle frame to a second opposing side of the buckle frame, a sliding arm configured to slide along the buckle frame. A buckle connector is attached to the compression strap to engage the buckle frame.

12 Claims, 9 Drawing Sheets

(56) References Cited

U.S. PATENT DOCUMENTS

| | | | |
|---|---|---|---|
| 10,258,347 B2* | 4/2019 | Hopman | A61B 17/1322 |
| 10,336,416 B2* | 7/2019 | Henderson | B63B 32/73 |
| 11,547,423 B2* | 1/2023 | Peterson | A61B 17/1322 |
| 11,684,373 B2* | 6/2023 | Parsons | A61B 17/1322 |
| | | | 606/203 |
| D991,452 S * | 7/2023 | Liu | D24/169 |
| 11,701,125 B2* | 7/2023 | Haskins | B63B 32/73 |
| | | | 606/203 |
| 11,826,053 B2* | 11/2023 | Johnson | A44B 11/18 |
| 2010/0057120 A1* | 3/2010 | Kirkham | A61B 17/1322 |
| | | | 606/203 |
| 2015/0216536 A1* | 8/2015 | Hopman | A61B 17/1322 |
| | | | 606/202 |
| 2016/0302799 A1* | 10/2016 | Esposito | A61B 17/1327 |
| 2016/0375969 A1* | 12/2016 | Henderson | A61B 17/1322 |
| | | | 606/203 |
| 2018/0228497 A1* | 8/2018 | Dimino | A61F 15/006 |
| 2020/0288820 A1* | 9/2020 | Johnson | A44B 11/06 |
| 2021/0000482 A1* | 1/2021 | Parsons | A61B 17/1322 |
| 2021/0153873 A1* | 5/2021 | Peterson | A61B 17/1322 |
| 2022/0151636 A1* | 5/2022 | Haskins | B63B 32/77 |
| 2022/0218359 A1* | 7/2022 | Johhnson | A61B 17/1322 |
| 2023/0233213 A1* | 7/2023 | Shedd | A61B 17/1322 |
| | | | 606/203 |

* cited by examiner

WINDLASS TOURNIQUET

This application claims the benefit of U.S. provisional patent application Ser. No. 62/845,051 filed on May 8, 2019, which is incorporated by reference herein in its entirety.

FIELD OF THE INVENTION

The present invention relates to the field of tourniquets.

BACKGROUND OF THE INVENTION

Uncontrolled hemorrhage from trauma remains a major cause of death, both on the battlefield and in civilian situations. Untreated, extreme bleeding as in the case of arterial bleeding can cause hypovolemic shock within just minutes.

Tourniquets are well-known devices used to stop blood loss from trauma. When properly deployed, they provide life-saving support in emergency situations when an injured victim is alone or cannot reach immediate medical attention. A standard tourniquet is a tightly tied or wound band applied around an injured limb in an attempt to increase pressure around the limb, above the injury and stop severe bleeding or uncontrolled hemorrhaging. Rapid application of a tourniquet above the site of injury is paramount to effective hemorrhage control, as is rapid incremental release of a tourniquet once medical assistance is available to provide next-step trauma management.

Many known tourniquets are of the "windlass" type. Such tourniquets typically include a strap threaded through a windlass handle and coupled to a tourniquet base. In order to tighten the tourniquet around the limb, the strap is threaded through a buckle and the windlass handle is twisted creating a knot between the windlass and the base and causing the strap to constrict circumferentially about the limb. It is important to apply and maintain sufficient pressure to the limb to occlude blood flow until the tourniquet is removed.

A drawback to some of these known tourniquets is that sometimes the knot created in the compression strap as the tourniquet handle is twisted becomes too bulky and the windlass tends to fall to one side, limiting the ability to further turn and create additional pressure. If the knot becomes too bulky, it may be difficult for the user to apply sufficient torque.

Even when the user is able to apply sufficient pressure, most windlass tourniquets experience pressure loss or creep of up to 25% during the first five minutes after the tourniquet is applied.

Accordingly, there is a need for a windlass tourniquet that facilitates the application of circumferential pressure and that compensates for natural pressure creep that occurs within minutes of tourniquet application.

SUMMARY OF THE INVENTION

In accordance with an embodiment of the invention, a tourniquet having a base including at least first and second sections and having a cap attached to one of the first and second sections is provided. A compression strap is attached to the base and extends across the base wherein a portion of the compression strap is sandwiched between the base and the cap. A windlass handle is provided and includes a strap aperture through which the compression strap is threaded through and stitched to itself by a stitch pattern so as to form a strap loop. A locking strap extends across and is attached to the cap. A handle stop engages the locking strap such that the handle stop and freely slides along the handle strap. A strap connector assembly is provided and includes a buckle frame and a self-cinching sliding arm transversely extending from a first side of the buckle frame to a second opposing side of the buckle frame, a sliding arm configured to slide along the buckle frame. The compression strap is threaded through said buckle frame, and a buckle connector is attached to the compression strap to engage the buckle frame.

In accordance with another embodiment of the invention, a tourniquet having a base including at least first and second sections and having a cap attached to one of the first and second sections is provided. A compression strap attached to said base and extends across the base wherein a portion of the compression strap is sandwiched between the base and the cap. A windlass handle is provided and includes a strap aperture through which compression strap is threaded and stitched to itself by a stitch pattern so as to form a strap loop. The stich pattern is centered along a width of the compression strap and has a widthwise dimension that is between ¼ to ½ of the width of the compression strap. A strap connector assembly is provided and includes a buckle frame and a self-cinching sliding arm transversely extending from a first side of the buckle frame to a second opposing side of the buckle frame, a sliding arm configured to slide along the buckle frame. The compression strap is threaded through said buckle frame, and a buckle connector is attached to the compression strap and configured to engage the buckle frame.

In accordance with an embodiment of the invention, a tourniquet having a base including at least first and second sections and having a cap attached to one of the first and second sections is provided. A compression strap is attached to the base and extends across the base wherein a portion of the compression strap is sandwiched between the base and the cap. A windlass handle is provided and includes a strap aperture through which the compression strap is threaded through and stitched to itself by a stitch pattern so as to form a strap loop. A locking strap extends across and is attached to the cap and is threaded through a handle stop which allows the handle stop to slide along the locking strap. A strap connector assembly is provided and includes a buckle frame and a self-cinching sliding arm transversely extending from a first side of the buckle frame to a second opposing side of the buckle frame, a sliding arm configured to slide along the buckle frame. The compression strap is threaded through said buckle frame, and a buckle connector is attached to the compression strap and configured to engage the buckle frame.

BRIEF DESCRIPTION OF THE DRAWINGS

Some embodiments of the present invention are illustrated as an example in the accompanying drawings and are described in sufficient detail to enable those skilled in the art to practice the invention. It is to be understood that other embodiments may be utilized and that structural changes based on presently known structural and/or functional equivalents may be made without departing from the scope of invention. The above and other objects, advantage and features of the present invention will be more readily apparent when read in conjunction with the following drawings wherein.

DETAILED DESCRIPTION OF THE INVENTION

Figure 1:
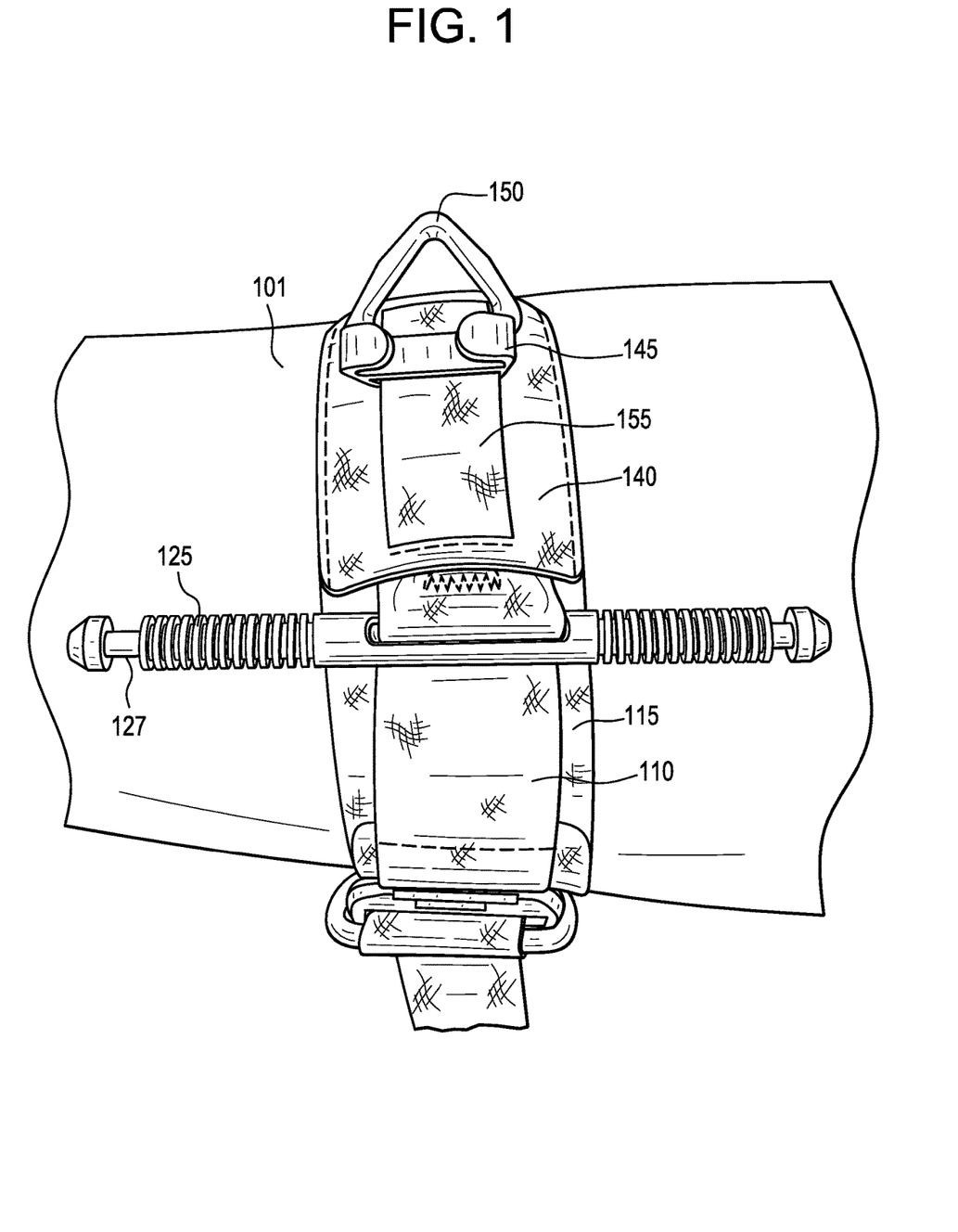
FIG. 1 depicts a top view of a tourniquet in accordance with an embodiment of the invention.

Now, referring to the FIGS. 1, a tourniquet 101 according to the invention includes a constricting band or compression strap 110 attached to/engaged with a base 115. Compression strap 110 preferably has a width of between about 1 inch and about 3 inches, and more preferably a width of between about 1 inch and about 2 inches. In an embodiment, compression strap 110 has a width of about 1.5 inches. Compression strap 110 has a length that, at a minimum, is sufficient to allow the strap to be wrapped around the limb of an average size adult male.

Base 115 is preferably wider than compression strap 110. In accordance with an embodiment of the invention, base 115 has a width of at least 2 inches.

A first end of compression strap 110 is fixedly attached, e.g., stitched, to base 115 at an attachment point proximate to a first end of base 115. Compression strap 110 extends across and parallel to the base 115 by a sufficient distance to, at a minimum, allow compression strap 110 to be wrapped around the limb of an average size adult male.

A tourniquet handle 125 is provided for tightening tourniquet 101. In some embodiments, tourniquet handle 125 is a windlass. In the illustrated embodiments, tourniquet handle 125 is generally cylindrical and may include locking grooves 127 disposed proximate first and second handle ends. In other embodiments, tourniquet handle 125 may be free from locking grooves.

Figure 2:
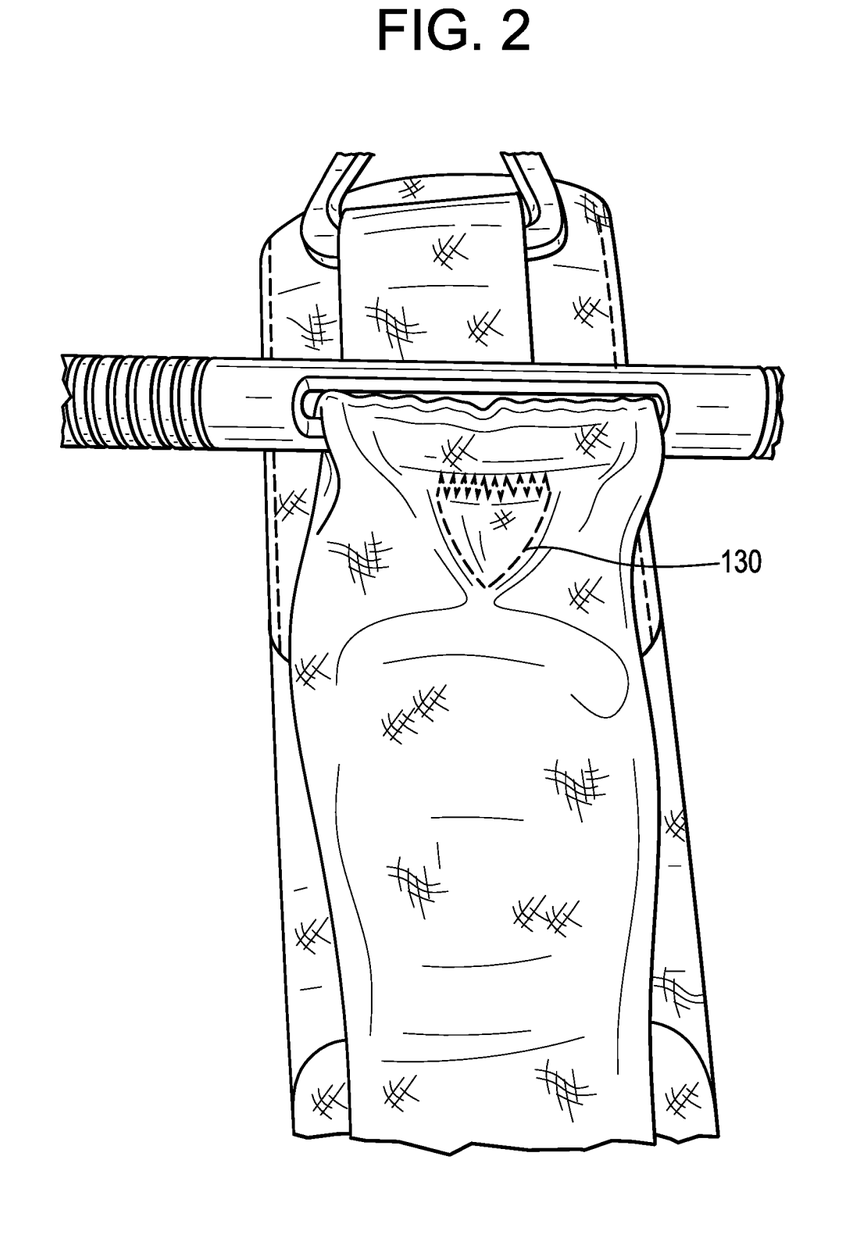
FIG. 2 is an exploded view of a tourniquet in accordance with an embodiment of the invention showing a stitch pattern.

Tourniquet handle 125 further includes an aperture through which compression strap 110 is threaded. As illustrated in FIG. 2, compression strap 110 is stitched to itself by a stitch pattern 130 to form a strap loop 135 which engages tourniquet handle 125. As tourniquet handle 125 is tightened, compression strap 110 accumulates and forms a twist or knot 135 (FIG. 3) which creates circumferential pressure. However, when the twist 135 is too bulky, tourniquet handle 125 has a tendency to fall to one side, thereby limiting the ability to continue to turn and create further circumferential pressure.

The present inventors have determined that the stitch pattern 130 impacts the size of twist 135. In keeping with the invention, stitch pattern 130 may be triangular where the triangle is generally centered along a width of compression strap 110 and the base of the triangle extends transversely along the width of compression strap 110 generally parallel to tourniquet handle 125 as illustrated in FIG. 2. In keeping with an aspect of the invention, stitch pattern 130 has a maximum widthwise dimension of between ¼ to ½ of the width of compression strap 110. In some embodiments, stitch pattern 130 may include various stitch patterns generally centered along the width of compression strap 110 including diamond, T, I and V shaped patterns. These patterns are believed to create different size twists but each is believed to markedly reduce the tendency of tourniquet handle 125 to fall to one side when it is tightened thereby making it easier to turn the handle and apply additional circumferential pressure.

A cap 140 overlays a portion of compression strap 110 and is fixedly attached to base 125 such that compression strap 110 is sandwiched between cap 140 and base 125. A handle stop 145 and a handle lock 150 are attached to cap 140 via locking strap 155 which is fixedly attached to cap 140 at first and second ends. Handle lock 150 is optional and may be omitted from all embodiments of the invention.

Figure 5:
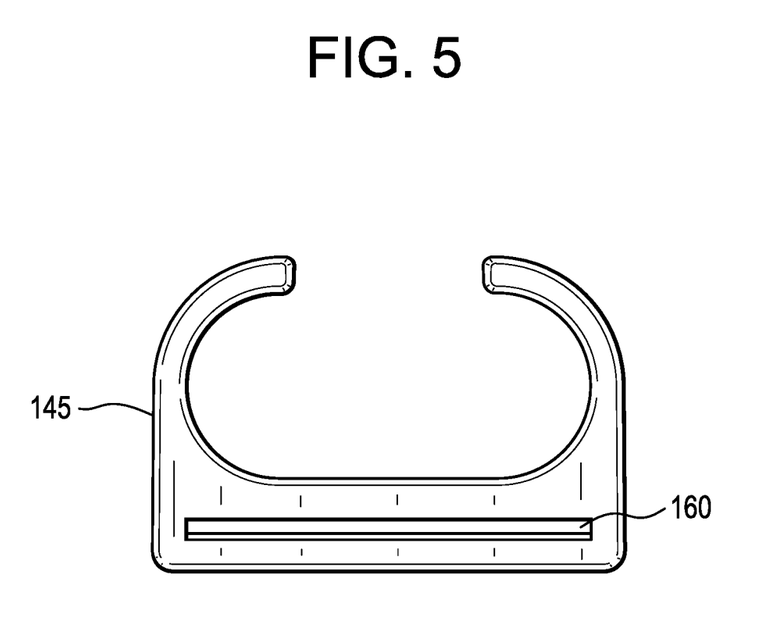
FIG. 5 shows a handle stop for a tourniquet of the present invention.

In accordance with an aspect of the invention, stop 145 and handle lock 150 are configured to slide freely along locking strap 155 between first and second ends. That is, both the lock 150 and the stop 145 are subject only to minimal friction forces exerted by locking strap 155 as they slide along locking strap 155. Neither lock 150 nor stop 145 are provided with any attachment mechanism to grip locking strap 155. As shown in FIG. 5, in one embodiment, handle stop 145 is a generally C-shaped member having a strap aperture 160. Locking strap 155 passes through strap aperture 160. Strap aperture 160 is sufficiently wide that at most only one of the upper boundary and the lower boundary of strap aperture 160 contact locking strap 155 at any given time thereby allowing handle stop 145 to freely slide. Lock 150 may comprise a ring, e.g., a triangle ring or a D-ring. Locking strap 155 passes through the ring opening thereby allowing lock 150 to freely slide.

Figure 3:
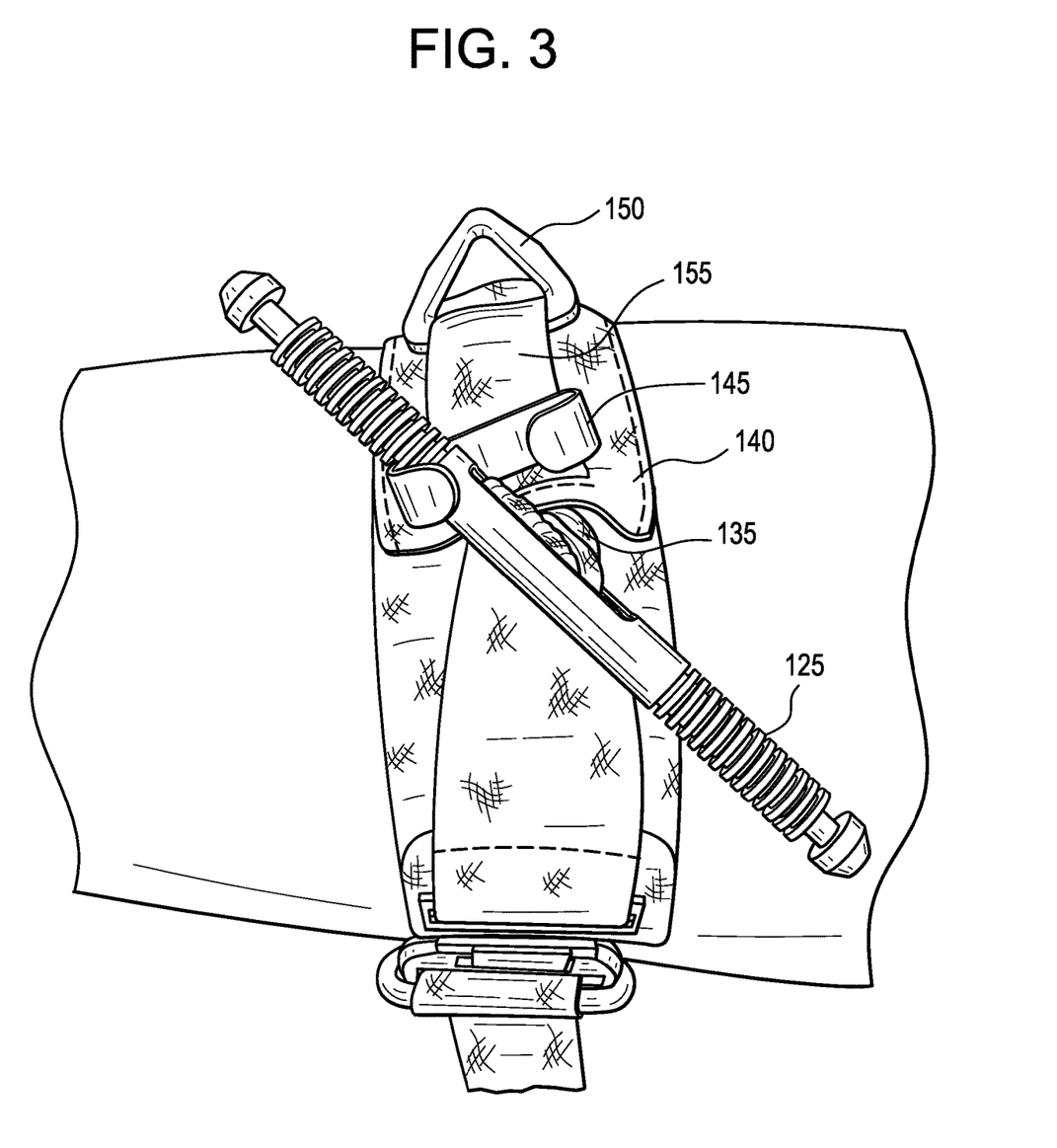
FIG. 3 illustrates a tourniquet in accordance with an embodiment of the invention applied to a limb in a first position.
Figure 4:
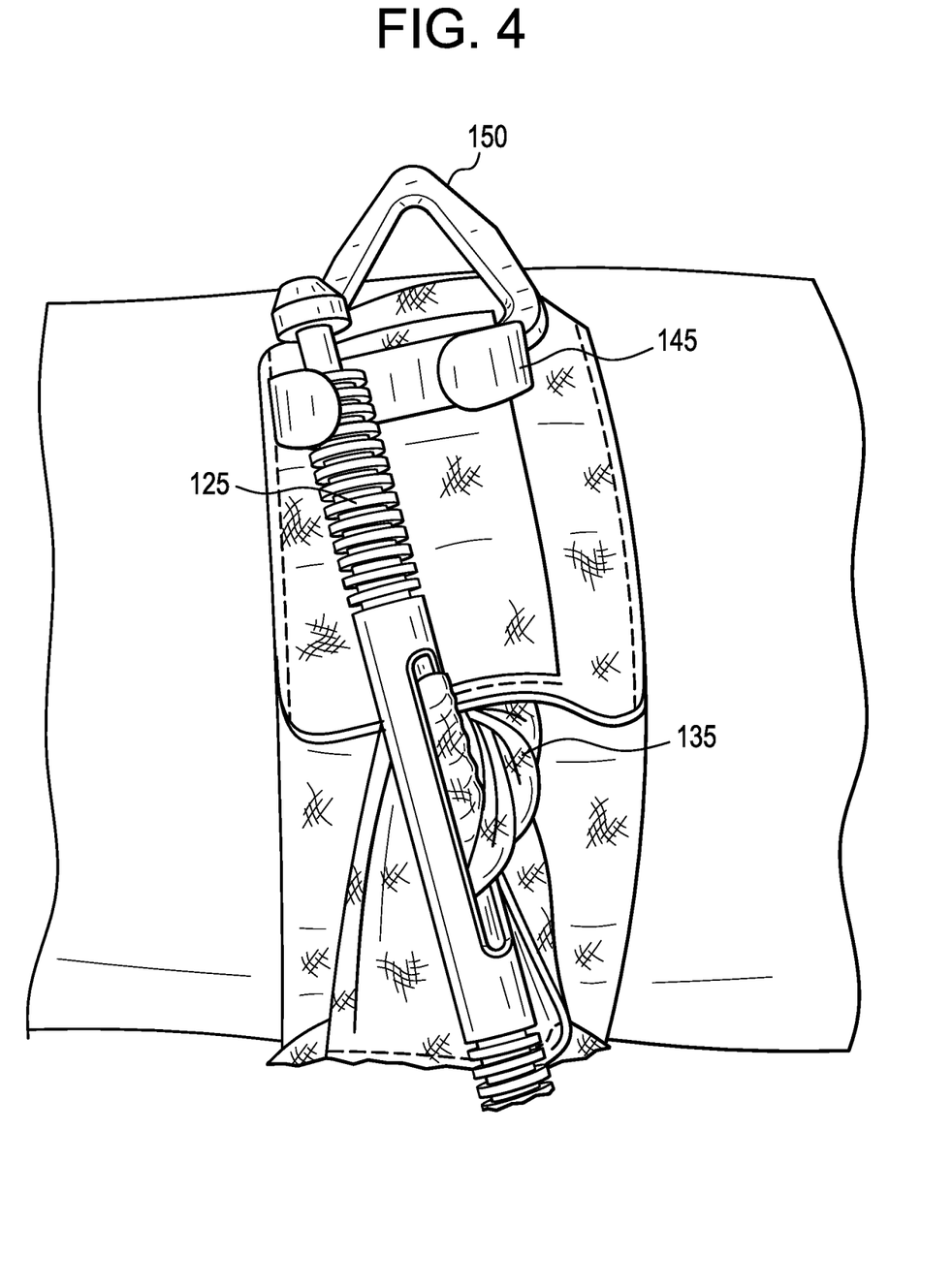
FIG. 4 depicts the tourniquet of FIG. 3 applying greater circumferential force.

In use, tourniquet handle 125 is twisted to generate a desired amount of torque and inserted into handle stop 145 to maintain the desired torque. Handle lock 150 may be engaged with one of the grooves formed proximate to an end of tourniquet handle 125 to lock tourniquet handle 125 in place. However, within about 5 minutes after tourniquet application, circumferential pressure loss of up to about 25% may occur due to weave stretch and settling. The present invention provides an advantage in that the user can increase pressure by up to about 25% without removing the tourniquet handle by sliding stop 145 and/or stop 150 up and away from twist 135. Illustrating this principle, FIG. 3 depicts tourniquet 101 secured in a first position where stop 145 is proximate to twist 135 and FIG. 4 illustrates tourniquet 101 secured in a second position where stop 145 has been slid away from twist 125.

In some embodiments, base 115 is substantially rigid and therefore maintains its integrity as tourniquet handle 125 is twisted. By substantially rigid, it is meant that base 115 is sufficiently rigid to avoid binding or crushing when tourniquet handle 125 is twisted while being flexible enough for use on a limb and facilitating tourniquet carriage and storage. In a particular embodiment, base 125 is made of a 2"×8½" section of central webbing member, a 2"×8½" of looped end Velcro® affixed to the underside of the central webbing member, and a 2"×3" strip of upper webbing member affixed to the upper side of the central webbing member. The central webbing member section may be made of a 16 point heavy weight polypropylene material or its equivalent. The upper webbing member may be made of nylon scuba webbing or its equivalent but each can be made of any other suitable material. For example, upper webbing member may be made of a plastic material. A nonskid or non-slip fabric or any other suitable material may be substituted for the looped end Velcro®.

The separate sections can be joined or combined by sewing, bonding or by using any suitable means. In the present embodiment, the looped end Velcro® section and the central webbing member are sewn together. The looped end of Velcro® is positioned so the bottommost layer of loop is in contact with the limb when the tourniquet 101 is used. Looped end of Velcro® is used in this embodiment to increase friction between the tourniquet 101 and the limb and to provide padding between the central webbing member and the tissue of the limb. Looped end of Velcro® also helps protect the skin and soft tissue from pinching and bruising that can be associated with the use of the tourniquet 101. Looped end of Velcro® also helps the user in applying tourniquet article 10 by holding the tourniquet in place and allowing the user to apply article 10 with one hand.

The upper webbing member may be attached to the upper facing side of the central webbing member about 2" in distance from the end of the upper webbing member and positioned beneath the handle 125. In some embodiments, nylon scuba webbing may be used for the upper webbing member to increase the rigidity of the base 115 and to minimize binding or crushing of base 115 when handle 125 is twisted or turned. In other embodiments, multiple sections of scuba webbing can be combined to form the upper webbing member, and this can further facilitate the needs of rigidity while still being flexible enough for use with a limb in addition to making tourniquet 101 easier to store and carry. The loop end Velcro® member, central webbing member and upper webbing member may each be constructed of scuba webbing and, each member of base 115 can be lengthened, shortened, narrowed or widened. Additional padding may also be added to base 115, or individually to loop end Velcro member, central webbing member or upper webbing member. One or more adhesive strips may also be used to bond one or more of the members comprising base 115.

Figure 6A:
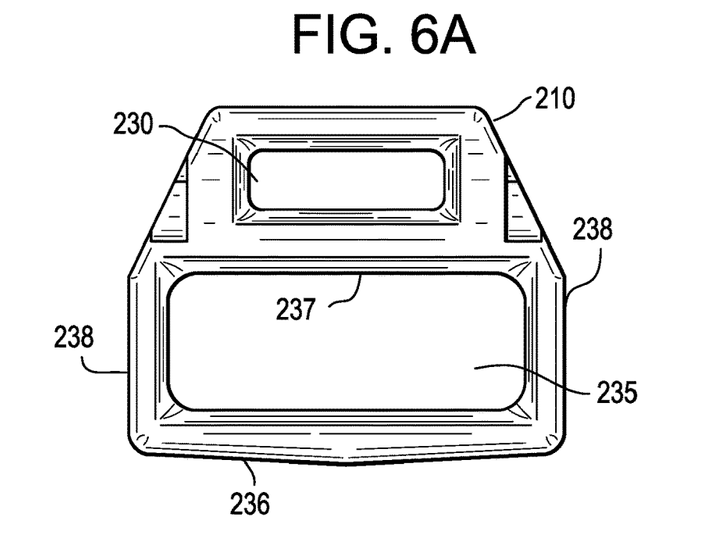
FIG. 6A shows a buckle frame in accordance with an embodiment of the invention.
Figure 6B:
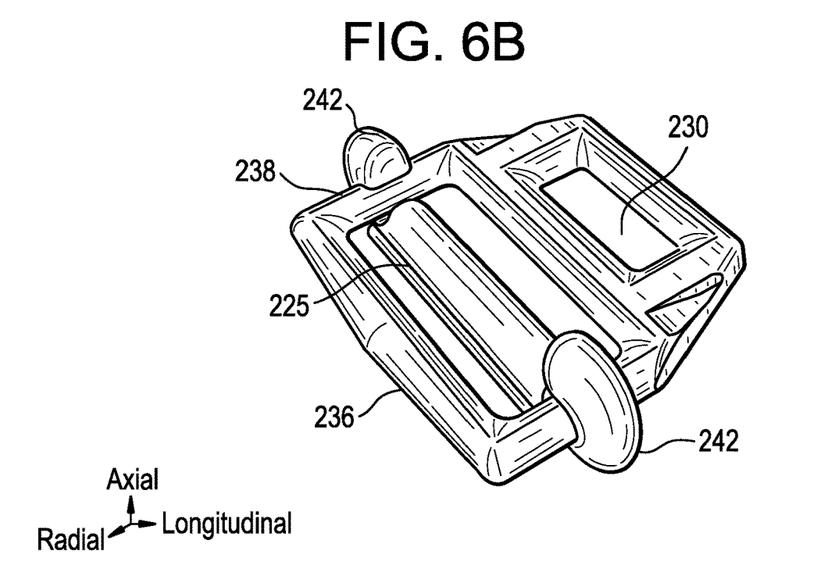
FIG. 6B shows a strap connection assembly in accordance with an embodiment of the invention.

In some embodiments, tourniquet 101 may include a strap connecting assembly 200 for releasably connecting compression strap 110 to itself. Strap connecting assembly 200 may include a slider buckle having a frame 210 with a self-cinching slide member 225 engaged with frame 210 and a buckle connector 220 attached to base 115 and configured to releasably engage frame 210. As depicted in FIG. 6, frame 210 includes a first aperture 230 configured to engage buckle connector 220 and a second aperture 235. Second aperture 235 is defined by first and second longitudinal sides 236 and 237 and first and second axial sides 238. In accordance with an aspect of the invention, self-cinching slide member 225 comprises a cuff or bar that extends across the second aperture 235 is externally mounted to first and second axial sides 238. Second aperture 235 is sized to minimize slippage and provide smooth strap take up. In accordance with an embodiment of the invention, second aperture 235 measures, for example, ¾"×1½".

While described above is particular embodiment of base 115, in keeping with the invention, base 115 may comprise other structures and materials and need not be substantially rigid.

Figure 6C:
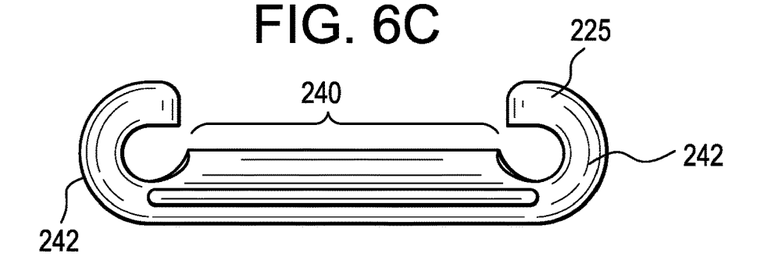
FIG. 6C illustrates a self-cinching sliding member in accordance with an embodiment of the invention.

Self-cinching slide member 225 includes a longitudinal center section 240 and first and second C-shaped end pieces 242. The first and second axial sides 238 fit snuggly within the crescent of the C-shaped end pieces allowing the self-cinching sliding bar to slide along opening in the axial direction. In keeping with the invention, self-cinching slide member 225 includes a strip gripping vane 244 that extends longitudinally from and protrudes radially along self-cinching member 225.

Figure 7:
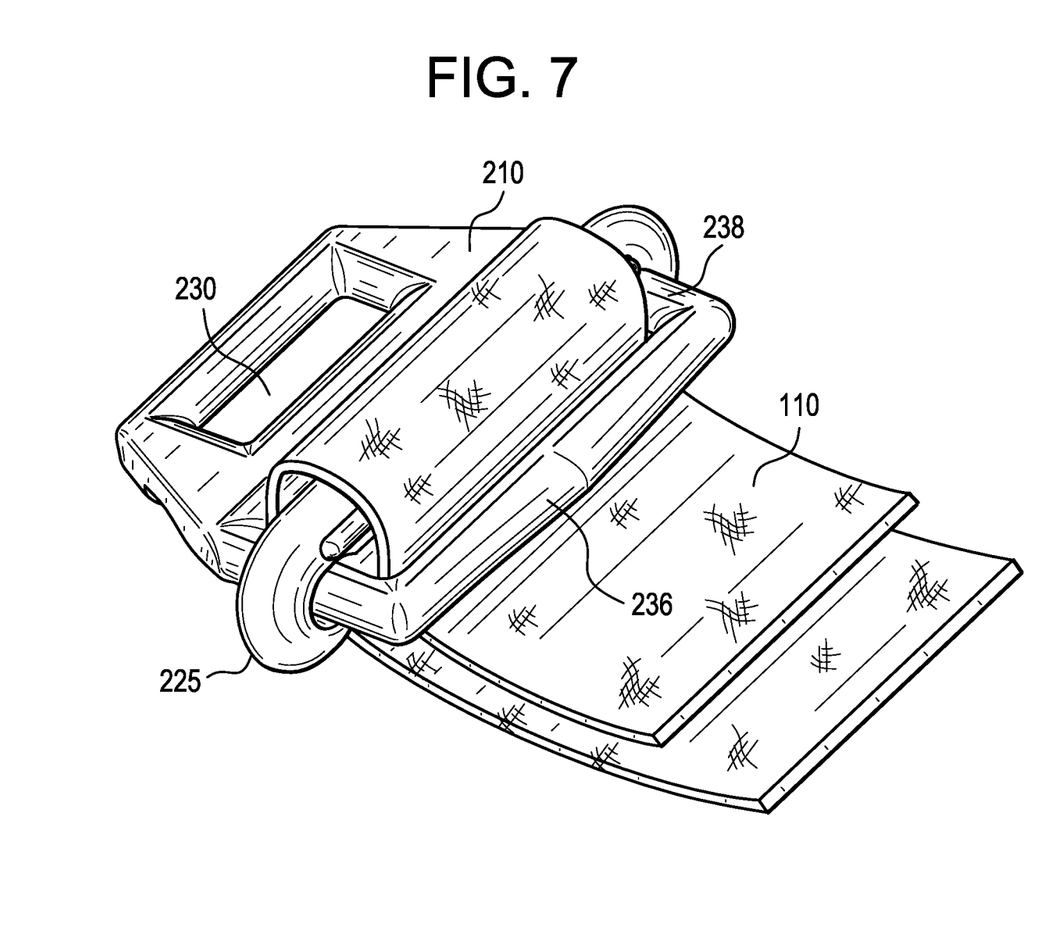
FIG. 7 depicts a strap connection assembly and strap combination in accordance with an embodiment of the invention.

As shown in FIG. 7, compression strap 110 is looped over self-cinching slide member 225 including over strap gripping vane 244 such that by simply pulling compression strap 110, the self-cinching slide member 225 slides along frame 210 until compression strap 110 is pinched between self-cinching slide member 225 and one of longitudinal sides 236 and 237. While not being bound by theory, it is believed that strap gripping vane 244 reduces strap slippage while under tension at angles of 45 degrees or less by altering the path of travel of compression strap 110.

In accordance with an aspect of the invention, buckle frame 210 and sliding member 225 are preferably comprised a material that is significantly more lubricious than metal yet strong enough to withstand forces normally encountered when using tourniquets. In some embodiments, buckle frame 210 and sliding member 225 comprises a glass fiber reinforced polyamide which can withstand pull tests of up to 300 lbs.

Figure 8:
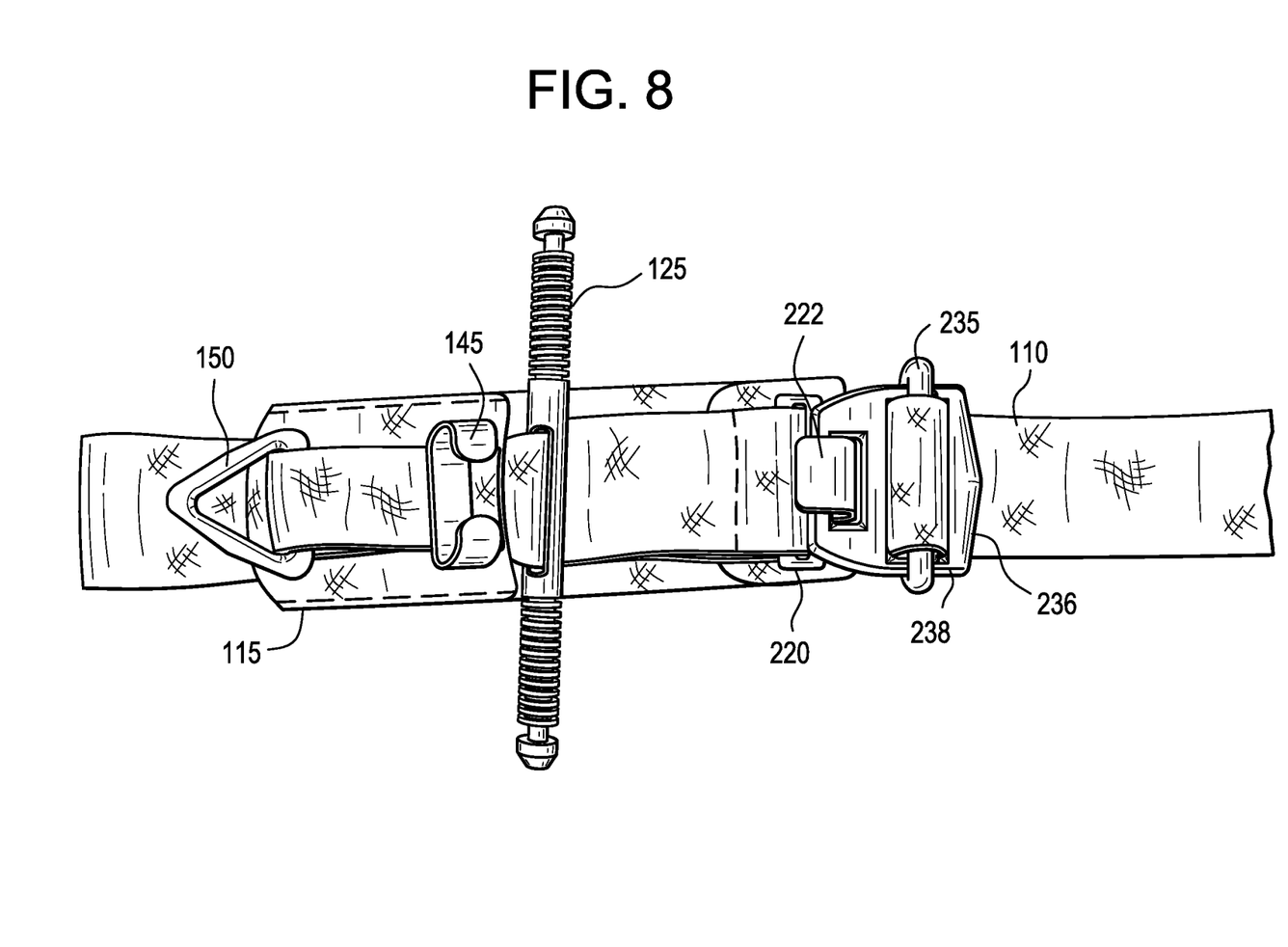
FIG. 8 shows a tourniquet in accordance with an embodiment of the invention.

Strap connector 220 comprises a hook member 222 and a strap channel base member 224 as shown in FIG. 8. Hook member 222 comprises a cuff having an interior surface. Hook member 222 extends from a strap channel base member 224 which defines a strap engaging aperture not shown in FIG. 8. Strap channel base member 224 may have edges and includes a first substantially vertical side from which hook member 222 extends and a second side which is slightly curved.

Figure 9:
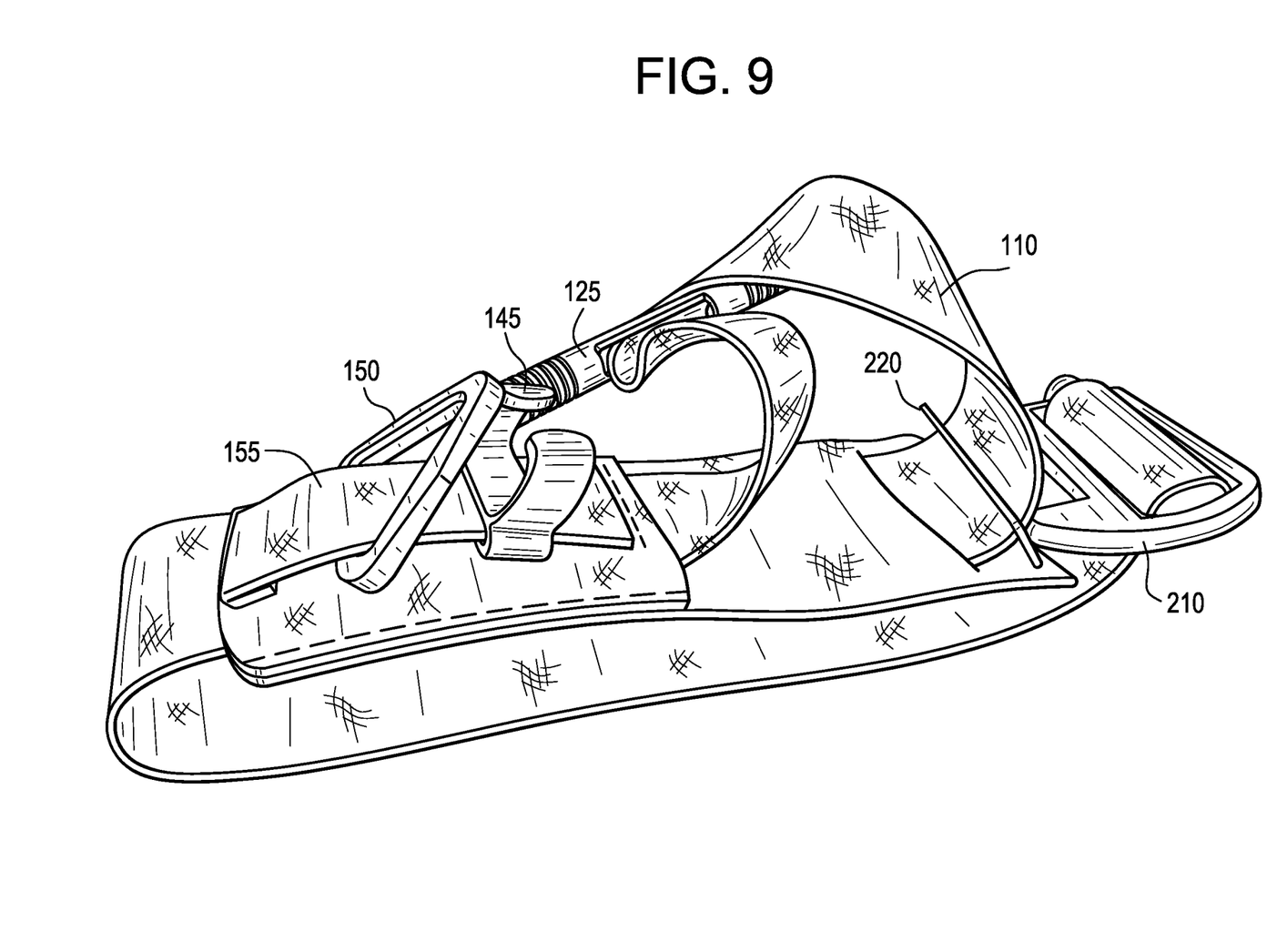
FIG. 9 shows a tourniquet in accordance with yet another embodiment of the invention.

In keeping with the invention, as illustrated in FIG. 9, compression strap 110 is threaded through buckle connector 220 and fixedly connected to base 125. This allows buckle connector 220 to slide freely along compression strap 110 between the point where compression strap 110 is attached to base 115 and stitch pattern 130. It is believed that allowing buckle connector 220 to freely slide creates a mechanical advantage of up to 2:1 which reduces torque and makes the tourniquet easier to use particularly for users with weak grip strength.

In a further embodiment to any of the embodiments discussed above, the strap connecting assembly 220 may be substituted for strap connecting assemblies described in U.S. Patent Publication No. 20110307004 A1 or 2018175953 A1 or for any similar such assembly. In addition, any windlass handle having a central aperture may be substituted for windlass handle 125.

Although particular materials have been identified for particular components and structural elements, one of ordinary skill in the art will appreciate that other materials may be substituted without departing from the scope of the invention. In at least one embodiment, slider buckle, the slide member and the buckle connector may comprise metal or plastic.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the root terms "include" and/or "have", when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means plus function elements in the claims below are intended to include any structure, or material, for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention.

[As used above "substantially," "generally," and other words of degree are relative modifiers intended to indicate permissible variation from the characteristic so modified. It is not intended to be limited to the absolute value or characteristic which it modifies but rather possessing more of the physical or functional characteristic than its opposite, and preferably, approaching or approximating such a physical or functional characteristic.

Those skilled in the art will appreciate that various adaptations and modifications of the embodiments described above can be configured without departing from the scope and spirit of the invention. Therefore, it is to be understood that, within the scope of the appended claims, the invention may be practiced other than as specifically described herein.

What is claimed is:

1. A tourniquet comprising:
   a base including at least first and second sections and having a cap attached to one of the first and second sections;
   a compression strap attached to said base and extending across said base, a portion of said compression strap being sandwiched between said base and the cap;
   a windlass handle having a strap aperture, said compression strap being threaded through said strap aperture and stitched to itself by a stitch pattern so as to form a strap loop;
   a locking strap extending across and attached to said cap;
   a handle stop engaging said locking strap such that said handle stop freely slides along said handle strap; and
   a strap connector assembly including a buckle frame and a self-cinching sliding arm transversely extending from a first side of the buckle frame to a second opposing side of the buckle frame, a sliding arm being configured to slide along the buckle frame, said compression strap being threaded through said buckle frame, and a buckle connector attached to said compression strap configured to engage said buckle frame.

2. The tourniquet of claim 1 wherein said stitch pattern includes one of a triangle, diamond, I, T and V pattern generally centered along a width of said compression strap.

3. The tourniquet of 2 wherein the said compression strap has a first width and said stitch pattern is centered about a center of the first width.

4. The tourniquet of claim 3 wherein the stitch pattern has a maximum widthwise dimension that is between ½ to ¼ of the first width of said compression strap.

5. The tourniquet of claim 1 further comprising a handle lock slidably engaged with said locking strap.

6. The tourniquet of claim 1 wherein said buckle connector is attached to said compression strap such that said buckle connector is capable of sliding along said compression strap between the point where said compression strap is attached to said base and said stitch pattern when said windlass handle is turned.

7. A tourniquet comprising:
   a base including at least first and second sections and having a cap attached to one of the first and second sections;
   a compression strap attached to said base and extending across said base, a portion of said compression strap being sandwiched between said base and the cap;
   a windlass handle having a strap aperture, said compression strap being threaded through said strap aperture and stitched to itself by a stitch pattern so as to form a strap loop, the stich pattern being centered along a width of said compression strap and having a widthwise dimension that is between ¼ to ½ of the width of said compression strap; and
   a strap connector assembly including a buckle frame and a self-cinching sliding arm transversely extending from a first side of the buckle frame to a second opposing side of the buckle frame, a sliding arm being configured to slide along the buckle frame, said compression strap being threaded through said buckle frame, and a buckle connector attached to said compression strap configured to engage said buckle frame.

8. The tourniquet of claim 7 wherein said stitch pattern is triangular.

9. The tourniquet of claim 7 wherein said stitch pattern includes one of, a diamond, an I, a T and a V.

10. A tourniquet comprising:
    a base including at least first and second sections and having a cap attached to one of the first and second sections;
    a compression strap attached to said base and extending across said base, a portion of said compression strap being sandwiched between said base and the cap;
    a windlass handle having a strap aperture, said compression strap being threaded through said strap aperture and stitched to itself by a stitch pattern so as to form a strap loop;
    a locking strap extending across and attached to said cap;
    a handle stop including an aperture, said locking strap being threaded through the aperture to allow said handle stope to slide along said locking strap; and
    a strap connector assembly including a buckle frame and a self-cinching sliding arm transversely extending from a first side of the buckle frame to a second opposing side of the buckle frame, a sliding arm being configured to slide along the buckle frame, said compression strap being threaded through said buckle frame, and a buckle connector attached to said compression strap configured to engage said buckle frame.

11. The tourniquet of claim 10 further comprising a handle lock slidably engaged with said locking strap.

12. The tourniquet of claim 10 wherein said buckle connector is slidably engaged with said compression strap.

* * * * *